United States Patent
Seong et al.

(10) Patent No.: US 11,866,693 B2
(45) Date of Patent: Jan. 9, 2024

(54) METHOD FOR IMMOBILIZING MALODOROUS MICROORGANISMS ON SURFACE OF EVAPORATOR

(71) Applicants: HYUNDAI MOTOR COMPANY, Seoul (KR); KIA MOTORS CORPORATION, Seoul (KR)

(72) Inventors: Kwangmo Seong, Bucheon-si (KR); Heungsik Kim, Seoul (KR); Mi Jung Yun, Yongin-si (KR)

(73) Assignees: HYUNDAI MOTOR COMPANY, Seoul (KR); KIA MOTORS CORPORATION, Seoul (KR)

(*) Notice: Subject to any disclaimer, the term of this patent is extended or adjusted under 35 U.S.C. 154(b) by 664 days.

(21) Appl. No.: 17/061,617

(22) Filed: Oct. 2, 2020

(65) Prior Publication Data
US 2021/0403896 A1    Dec. 30, 2021

(30) Foreign Application Priority Data
Jun. 30, 2020   (KR) .......................... 10-2020-0079749

(51) Int. Cl.
| | |
|---|---|
| C12N 11/00 | (2006.01) |
| A61L 2/232 | (2006.01) |
| B60H 1/32 | (2006.01) |
| C12Q 1/02 | (2006.01) |
| B60H 3/00 | (2006.01) |

(52) U.S. Cl.
CPC .............. *C12N 11/00* (2013.01); *C12Q 1/02* (2013.01); *A61L 2/232* (2013.01); *B60H 1/3227* (2013.01); *B60H 3/0092* (2013.01)

(58) Field of Classification Search
None
See application file for complete search history.

(56) References Cited

U.S. PATENT DOCUMENTS

| | | | |
|---|---|---|---|
| 2018/0303963 A1* | 10/2018 | Park ................... | B01D 53/84 |
| 2019/0119625 A1* | 4/2019 | Lee .................... | C12M 41/34 |

FOREIGN PATENT DOCUMENTS

KR   10-2018-0001311 A   1/2018

* cited by examiner

*Primary Examiner* — Michael P. Rodriguez
(74) *Attorney, Agent, or Firm* — MORGAN, LEWIS & BOCKIUS LLP

(57) ABSTRACT

The present disclosure relates to a method for pretreating an evaporator for accelerating odor reproduction of an odor reproduction device for a vehicle air conditioning system, and a method for pretreating an evaporator surface of the present disclosure may include: a step of preparing an inoculation of malodorous microorganisms; a step of preparing and pretreating an evaporator; and a step of immobilizing malodorous microorganisms on an evaporator surface.

8 Claims, 4 Drawing Sheets

Preparing inoculation of malodorous microorganisms (10)

Preparing and pretreating evaporator (20)

Immobilizing malodorous microorganisms (30)

METHOD FOR IMMOBILIZING MALODOROUS MICROORGANISMS ON SURFACE OF EVAPORATOR

CROSS-REFERENCE TO RELATED APPLICATION

The present application claims the benefit of priority to Korean Patent Application No. 10-2020-0079749 filed on Jun. 30, 2020 in the Korean Intellectual Property Office, the entire contents of which are incorporated herein by reference.

TECHNICAL FIELD

The present disclosure relates to a method for immobilizing malodorous microorganisms on a surface of an evaporator.

BACKGROUND

As quality of life improves along with economic growth, a consumer's interest in health and well-being is increasing, and accordingly, air quality regulations of an indoor such as multi-use facilities and vehicles are being strengthened.

Vehicle manufacturers are managing eight types of volatile organic compounds (VOCs) such as toluene to correspond to the indoor air quality regulations of new cars, and are also strengthening management by increasing application of odor-reducing materials to reduce odor complaints from consumers.

Recently, consumer's complaints about the odor of air vents from used cars are increasing along with volatile organic compounds (VOCs)/smells of new cars.

That is, the unpleasant smell from the air vents of used cars is largely caused by the following three factors.

First, when an air conditioning system (Heating, Ventilation, Air Conditioning: HVAC) is operated in an outdoor air mode, the unpleasant smell may be due to an inflow of odorous components in the environment such as smoke and manure smells. Second, the odor components may flow into the air-conditioning system from the outside/indoor, and may be adsorbed on air-conditioning parts such as a filter, then desorbed. Third, the unpleasant smell may occur when odor-causing microorganisms flow into the air-conditioning system and are attached to air-conditioning parts such as an evaporator, and microorganism volatile organic compounds (mVOCs) of metabolic byproducts are produced through biofilm formation and metabolic activity.

Accordingly, vehicle manufacturers and air-conditioning partners are expanding the development and application of combination filters to which activated carbon added, ionizers with sterilization and deodorization functions, and antibacterial is coating evaporators to suppress the growth of microorganisms to reduce unpleasant odors in air vents.

However, despite the improvement efforts, consumer's complaints about the unpleasant smell from the air vents are still increasing. It has been determined that the increase in consumer's complaints, such as deterioration of a vehicle dependability study (VDS) quality index for the unpleasant odors from air vents, is attributed to improper evaluation of an odor improvement effect along with product performance evaluation of an odor reduction technology.

Therefore, in order to evaluate the improvement effect of the odor reduction technology, there is a need to develop an odor reproduction device reflecting consumer's use conditions.

The above information disclosed in this Background section is to aid in the understanding of the background of the present disclosure, and therefore should not be taken as acknowledgement that this information forms any part of prior art.

SUMMARY

The present disclosure intends to provide an evaporator pretreatment method for accelerating odor reproduction of an odor reproduction device in a vehicle air conditioning system that enables a field environment and a vehicle condition to be implemented to evaluate an odor improvement effect of an air conditioning system reflected with an odor reduction technology.

A method for pretreating an evaporator surface of an exemplary embodiment of the present disclosure may include: a step of preparing an inoculation of malodorous microorganisms; a step of preparing and pretreating an evaporator; and a step of immobilizing malodorous microorganisms on an evaporator surface.

The step of preparing the inoculation of malodorous microorganisms may include: a step of preparing malodorous microorganisms; a step of preparing an LB broth liquid medium; a step of liquid-cultivating malodorous microorganisms in the LB broth liquid medium; and a step of concentrating and recovering the cultivated malodorous microorganisms.

The step of preparing and pretreating the evaporator may include: a step of closing and sealing a refrigerant pipe of the evaporator; a step of treating a flowing stream of the evaporator of which the refrigerant pipe is closed and sealed; and a step of drying the evaporator of which the flowing stream is treated.

The step of treating the flowing stream of the evaporator may include a step of installing the evaporator to a flowing stream treatment device and treating the flowing stream to cleanse the surface, and the flowing stream treatment device may include a square box, an evaporator holder, a tap water inlet, and a tap water outlet. Specifically, the washing water may be a tap water.

The step of immobilizing malodorous microorganisms on the surface of the evaporator may include: a step of preparing a liquid mixture of malodorous microorganisms; a step of spraying the liquid mixture of malodorous microorganisms; and a step of drying the evaporator on which the liquid mixture of malodorous microorganisms is sprayed.

In the step of immobilizing malodorous microorganisms on the surface of the evaporator, the step of spraying the liquid mixture and the step of drying the evaporator may be sequentially repeated twice or more. The step of spraying the liquid mixture and the step of drying the evaporator may be sequentially repeated 3 to 4 times.

The method may further include a step of producing a biofilm after the step of immobilizing malodorous microorganisms on the surface of the evaporator.

The step of producing the biofilm may include: a step of preparing an LB broth nutrient; a step of spraying the LB broth nutrient; and a step of drying and culturing the evaporator on which the nutrient is sprayed.

In the step of producing the biofilm, the step of spraying the LB broth nutrient and the step of drying and culturing the evaporator may be sequentially repeated twice or more. The step of spraying the LB broth nutrient and the step of drying and culturing the evaporator may be sequentially repeated 5 to 7 times.

According to an embodiment of the present disclosure, an odor effect evaluation by microorganism proliferation of the evaporator surface and metabolic byproduct generation is possible, and a short-term accelerated evaluation is possible to achieve a purpose of the odor reproduction device of the vehicle air conditioning system, thereby allowing the odor reproduction reflecting field conditions.

According to one embodiment of the present disclosure, it is possible to synthetically evaluate a system unit and to evaluate an odor reduction contribution degree for each part/technology.

According to an embodiment of the present disclosure, a comprehensive comparison evaluation of the HVAC module unit may be possible.

According to an embodiment of the present disclosure, It is possible to evaluate the odor effect depending on an aging state and the presence/absence of the malodorous microorganisms activation, and it is possible to evaluate the effect of the evaporator improvement, for example, an easy drainage structure and a new antibacterial coating, thereby an evaporator odor reduction contribution is possible.

Ultimately, according to an embodiment of the present disclosure, it is possible to contribute to enhancing an emotional quality through strengthening verification of an improvement effect of an odor reduction technology.

DETAILED DESCRIPTION OF THE EMBODIMENTS

The technical terms used herein are to simply mention a particular embodiment and are not meant to limit the present disclosure. An expression used in the singular encompasses an expression of the plural, unless it has a clearly different meaning in the context. In the specification, it is to be understood that the terms such as "including", "having", etc., are intended to indicate the existence of specific features, regions, numbers, stages, operations, elements, components, and/or combinations thereof disclosed in the specification, and are not intended to preclude the possibility that one or more other specific features, regions, numbers, operations, elements, components, and/or groups may exist or may be added.

The present disclosure will be described more fully hereinafter with reference to the accompanying drawings, in which exemplary embodiments of the invention are shown, so as to be easily understood by a person with ordinary skill in the art. As easily understood by a person with ordinary skill in the art to which the present disclosure pertains, the exemplary embodiments which will be described below may be variously modified without departing from the spirit and the scope of the present disclosure. As those skilled in the art would realize, the described embodiments may be modified in various different ways, all without departing from the spirit or scope of the present disclosure.

An exemplary embodiment of the present disclosure relates to a method for immobilizing an evaluation strain on an evaporator surface to supplement a vehicle air conditioning system odor reproduction device capable of reproducing an air conditioning odor by realizing a normal atmosphere environment condition (temperature, humidity, dust, microorganisms, a pollution gas, etc.), a vehicle condition (EVA core cooling by a refrigerant, heater core heating by hot water), and a user condition (an A/C use pattern, etc.) when an HVAC (heating, ventilation, air conditioning) module is applied to odor reproduction evaluation and an air conditioning system is exposed while a vehicle is operated and stopped.

Figure 1:
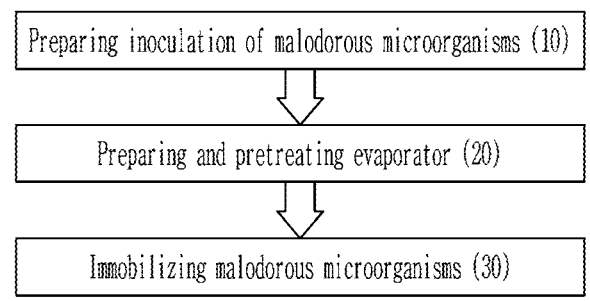
FIG. 1 is a flowchart of an evaporator pretreatment method for accelerating odor reproduction of an odor reproduction device of a vehicle air conditioning system according to an exemplary embodiment of the present disclosure.

FIG. 1 of the present disclosure is a schematic view of a method for immobilizing of an evaporator surface evaluation strain and shows a step 10 of preparing a malodorous microorganism inoculation, a step 20 of preparing and pretreating an evaporator, and a step 30 of immobilizing malodorous microorganisms.

The step 10 of preparing the malodorous microorganisms inoculation may include a step 11 of preparing malodorous microorganisms, a step 12 of preparing an LB broth liquid medium, as known as LB medium, Lysogeny broth, Luria broth, or Luria-Bertani medium, a step 13 of liquid-cultivating malodorous microorganisms in the LB broth liquid medium, and a step 14 of concentrating and recovering the cultivated malodorous microorganisms.

In the step 11 of preparing malodorous microorganisms, 12 types of malodorous-causing bacteria detected in an HVAC of an air conditioning odor generating vehicle are used. 12 types of malodorous-causing bacteria are inoculated in an agar solid medium and purely cultivated for 5 to 7 days in a 30° C. incubator.

In the step 12 of preparing the LB broth liquid medium, 2 L are prepared with a composition made by adding 25 g of LB broth per 1 L of tertiary distilled water and divided into 100 mL portions in twelve 250 mL Erlenmeyer flasks, and an inlet is sealed with a sili stopper and aluminum foil. The Erlenmeyer flask is placed in a high-pressure sterilizer, and the medium is sterilized at 120° C. for 15 minutes, and then taken out of the high-pressure sterilizer and cooled to room temperature.

In the step 13 of liquid-cultivating malodorous microorganisms in the LB broth liquid medium, the malodorous microorganisms cultivated in the agar solid medium are inoculated into a liquid medium by using a platinum loop. The platinum loop is heated by an alcohol lamp before use to be sterilized, and also heated by the alcohol lamp after use to be sterilized. The Erlenmeyer flasks respectively inoculated with 12 types of malodorous microorganisms are cultivated for about 3-4 days in a shaking incubator at 30° C. and at 150 rpm.

In the step 14 of concentrating and recovering the cultivated malodorous microorganisms, 12 types of malodorous microorganism concentrated culture solutions are divided into 50 ml centrifuge tubes and treated at 4° C. and at 10,000±2000 rpm for 10 minutes using a centrifugal separator, and a supernatant solution is carefully removed using a pipette. Each centrifuge tube is filled with a sterilized 0.82% NaCl solution to be 50 ml and refrigerated and stored at 4° C. before being inoculated in an evaporator.

The step 20 of preparing and pretreating the evaporator may include a step 21 of closing and sealing an evaporator refrigerant pipe, a step 22 of treating a flowing stream of the evaporator of which the refrigerant pipe is closed and sealed, and a step 23 of drying the evaporator of which the flowing stream is treated.

In the step 21 of closing and sealing the evaporator refrigerant pipe, in the process of treating the flowing stream, the evaporator refrigerant pipe is tightly closed and sealed using a lab wrap or Teflon tape to prevent moisture from flowing into the refrigerant pipe of the evaporator. This is a measure to prevent a cooling apparatus failure during a reproduction evaluation due to moisture inflow.

Figure 2:
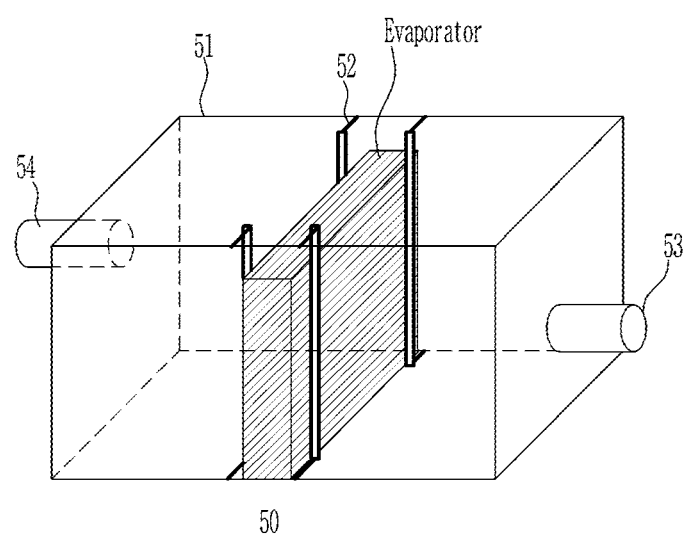
FIG. 2 is a schematic view of a flowing stream treatment device 50 according to an exemplary embodiment of the present disclosure.

In the step 22 of treating the flowing stream of the evaporator of which the refrigerant pipe is closed and sealed, the evaporator is installed on a flowing stream treatment device 50 as shown in FIG. 2. The flowing stream treatment device 50 includes a square box 51 made of a plastic or metal material, an evaporator holder 52 for mounting the evaporator in the device 50, a tap water inlet 53, and a tap water outlet 54. In this step, tap water flows at 2 L per minute for 72 hours via the tap water inlet 53 and the tap water outlet 54. This is a measure to accelerate the odor reproduction by removing a surfactant component of the evaporator surface and aging a hydrophilic coating layer to facilitate attachment of microorganisms and gas adsorption.

In the step 23 of drying the evaporator treated with the flowing stream, the evaporator is removed from the flowing stream treatment device after flowing stream treatment, drained vertically for 24 hours, then horizontally mounted for 24 hours or more, and then dried sufficiently under a room temperature condition.

Figure 3:
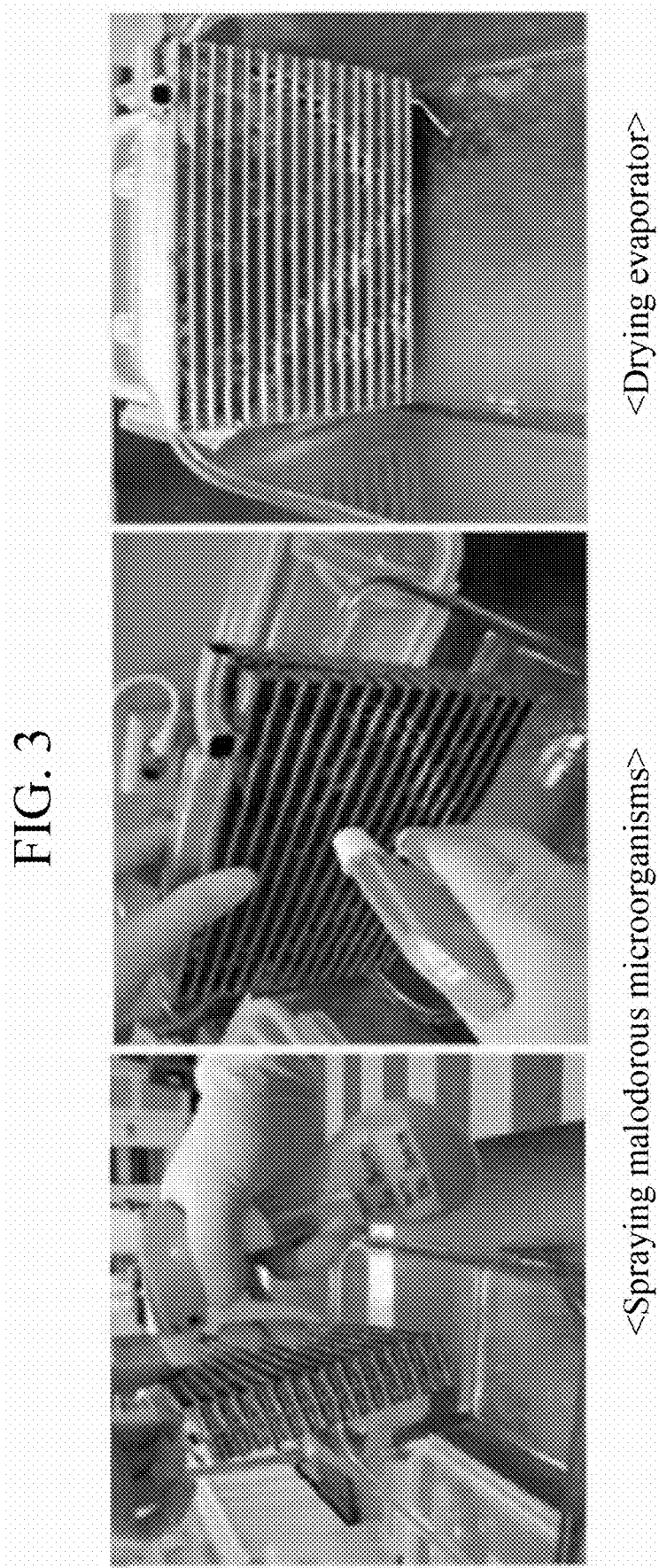
FIG. 3 is a view showing a liquid mixture spraying step and an evaporator drying step among a step of immobilizing malodorous microorganisms on an evaporator surface according to an exemplary embodiment of the present disclosure.

The step 30 of immobilizing the malodorous microorganisms on the surface of the evaporator may include a step 31 of preparing a liquid mixture of the malodorous microorganisms, a step 32 of spraying the liquid mixture of the malodorous microorganisms, and a step 33 of drying the evaporator on which the liquid mixture of the malodorous microorganisms is sprayed. The step 32 of spraying the liquid mixture and the step 33 of drying the evaporator may be repeated 3 to 4 times to attach the malodorous microorganisms to the surface of the evaporator (referring to FIG. 3).

In the step 31 of preparing the liquid mixture of the malodorous microorganisms, a concentrated solution for each malodorous bacteria is mixed in a 5 L beaker, the liquid mixture of the malodorous bacteria and an 0.82% NaCl solution are diluted at 1:2, and fine dust (A2 fine dust) is added to be 1.5 g/L and then mixed by being sufficiently stirred for 1 hour. The reason for adding the fine dust is to suppress contact between malodorous-causing bacteria and an antibacterial agent of the coating surface of the evaporator and to facilitate the attachment of bacteria to the surface of the evaporator.

In the step 32 of spraying the liquid mixture of the malodorous microorganisms, in a state that the evaporator is vertically mounted inside a fume hood in which a blow fan is operated, 100 ml of the liquid mixture is sprayed on the front and back sides for each evaporator. At the bottom of the evaporator, a tray capable of recovering the liquid mixture sprayed on the evaporator is installed, and the collected liquid mixture is sprayed again on the front and back sides of the evaporator.

In the step 33 of drying the evaporator on which the liquid mixture of the malodorous microorganisms is sprayed, in the state that the evaporator is vertically mounted inside the fume hood in which the blow fan is operated, the evaporator is dried for 3-4 hours. The liquid mixture spraying and evaporator drying are repeated 3-4 times over 2 days, but during the night time passing from day 1 to day 2, the evaporator is sealed in a zipper bag and stored in an incubator at 30° C.

Figure 4:
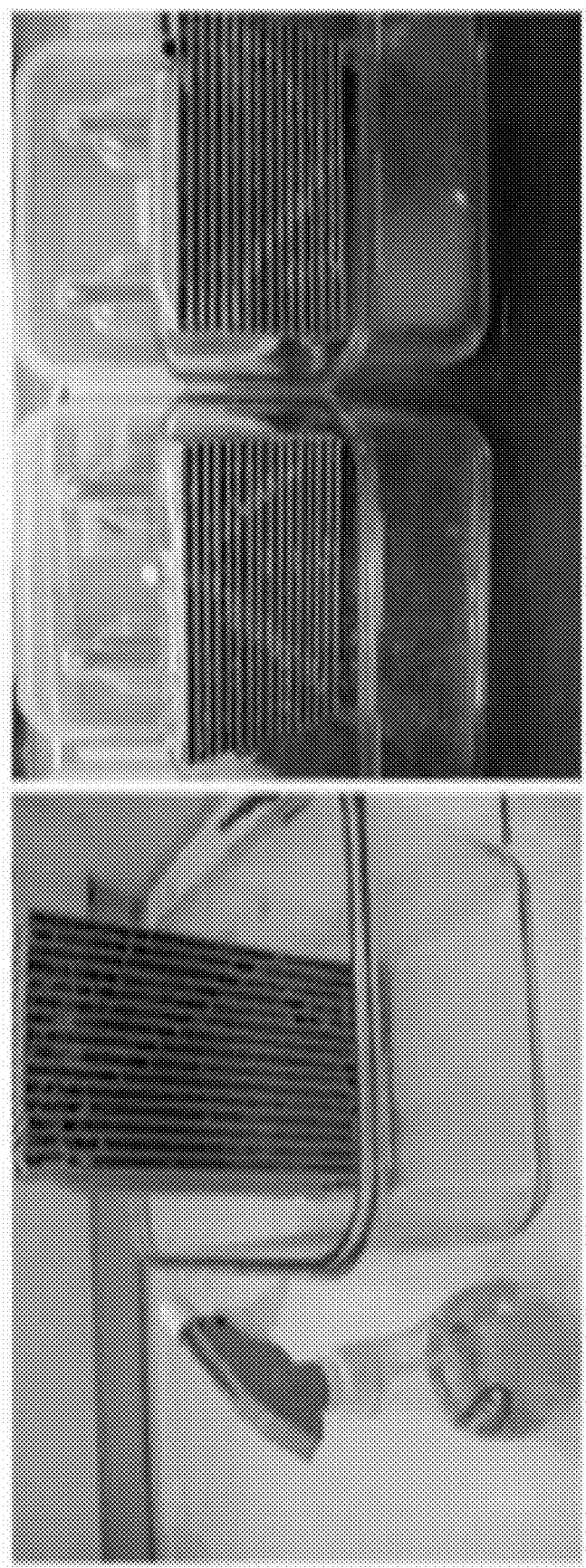
FIG. 4 is a view showing a nutrient spraying step and an evaporator drying and culturing step among a biofilm producing step according to an exemplary embodiment of the present disclosure.

A step 40 of producing a biofilm may be further included after the step 30 of immobilizing the malodorous microorganisms on the surface of the evaporator. The step 40 of producing the biofilm may include a step 41 of preparing an LB broth nutrient, a step 42 of spraying the LB broth nutrient, and a step 43 of drying and culturing the evaporator on which the nutrient is sprayed. In the step of producing the biofilm, the step 42 of spraying the nutrient and the step 43 of drying and culturing the evaporator may be repeated 5 to 7 times to activate the malodorous microorganisms to be fixed on the surface of the evaporator surface (referring to FIG. 4).

In the step 41 of preparing the LB broth nutrient, 4 ml of the LB broth liquid medium prepared in the inoculation preparing step 10 is added to a 0.82% NaCl solution to make 1 L of 0.1% LB broth nutrient, and the mixture is thoroughly stirred for 1 hour.

In the step 42 of spraying the LB broth nutrient in the state that the evaporator is vertically mounted inside the fume hood in which the blow fan is operated, the 50 ml of liquid mixture is sufficiently sprayed on the front and back sides of the evaporator. At the bottom of the evaporator, a tray capable of recovering the nutrient sprayed on the evaporator is installed, and the collected nutrient is sprayed again on the front and back sides of the evaporator.

In the step 43 of drying and culturing the evaporator on which the nutrient is sprayed, in the state that the evaporator is vertically mounted inside the fume hood in which the blow fan is operated, the evaporator is sealed in a zipper bag after being dried for 3-4 hours and stored in an incubator at 30° C. The spraying of the nutrient and the drying/cultivating of the evaporator are repeated daily for 5-7 days to activate the malodorous microorganisms and fix them on the evaporator surface.

An air conditioning odor reproduction evaluation is performed for 2 months using the evaporator in which the microorganisms are cultivated by the above-described method, and the results are shown in Table 1 below.

In Table 1 below, the concentration (ppm, "Pars Per Million") of each odor material is measured twice using an air conditioning odor reproduction device using an evaporator prepared by an existing method and an evaporator prepared by the present exemplary embodiment method, respectively. In addition, the concentration for each odor material of three types of used car is measured.

TABLE 1

| Identification | | Minimum detected concentration [ppm] | Reproduction device [ppm] | | | | Used car [ppm] | | |
|---|---|---|---|---|---|---|---|---|---|
| Classification | Odor material name | | Existing first | Existing second | Improvement first | Improvement second | Type1 | Type2 | Type3 |
| Aldehydes | Acetaldehyde | 0.186 | 0.017 | 0.028 | 0.009 | 0.048 | 0.033 | 0.061 | 0.055 |
| | Propionaldehyde | 0.0087 | 0.002 | nd | nd | 0.004 | 0.006 | 0.012 | 0.006 |
| | Butyraldehyde | 0.00891 | 0.002 | nd | nd | nd | 0.004 | 0.007 | 0.004 |
| | Nonanal | 0.00224 | 0.002 | 0.001 | 0.001 | 0.001 | 0.005 | 0.011 | 0.009 |
| VOCs | 2-Butoxy ethanol | 0.046 | 0.016 | 0.162 | 0.013 | 0.122 | nd | 0.002 | 0.004 |
| | 2-Ethyl-1-hexanol | 0.246 | 0.005 | 0.001 | nd | 0.001 | 0.004 | 0.027 | 0.020 |
| | Methyl ethyl ketone | 0.44 | 0.003 | 0.015 | 0.007 | 0.008 | 0.009 | 0.003 | 0.003 |
| | Methyl Isobutyl ketone | 0.17 | 0.001 | 0.001 | nd | nd | 0.007 | 0.018 | 0.002 |
| | Acetone | 14.2 | nd | 0.002 | 0.005 | 0.001 | nd | nd | nd |
| | n-Butyl acetate | 0.196 | 0.001 | 0.001 | 0.001 | nd | 0.003 | 0.004 | 0.002 |
| | Ethyl acetate | 0.87 | 0.003 | 0.016 | 0.005 | 0.002 | 0.001 | nd | nd |
| | Toluene | 0.33 | 0.018 | 0.054 | 0.027 | 0.014 | 0.016 | 0.021 | 0.015 |
| | Styrene | 0.035 | 0.001 | 0.002 | 0.001 | nd | nd | 0.006 | 0.002 |
| | Xylene | 0.058 | 0.004 | 0.010 | 0.005 | 0.009 | 0.006 | 0.024 | 0.007 |
| | Ethyl benzene | 0.17 | 0.002 | 0.006 | 0.002 | 0.003 | 0.003 | 0.010 | 0.003 |
| | Octane | 1.7 | 0.001 | 0.001 | nd | nd | nd | 0.002 | n.d |
| | Nonane ② | 2.2 | nd | 0.002 | nd | 0.001 | nd | nd | nd |
| | Heptane | 0.67 | nd | 0.002 | 0.001 | nd | nd | 0.001 | nd |
| Organic acids | Acetic acid | 0.145 | 0.002 | nd | 0.001 | nd | nd | nd | nd |
| Amines | Tri-methyl amine | 0.00032 | nd | nd | 0.001 | nd | nd | nd | nd |
| Malodorous intensity (=Σdetected concentration/minimum detected concentration) | | | 2.0 | 2.5 | 4.0 | 4.2 | 3.8 | 4.8 | 5.9 |
| Functional evaluation | | | Unidentified/ 2.5 | Unidentified/ 2.5 | Water fishy smell/ 3.0 | Sour smell/ 3.0 | Water fishy smell/ 3.0 | Fishy smell/ 3.5 | Fishy smell/ 4.0 |

As confirmed from the results in Table 1, the concentration and the malodorous intensity of the malodorous material in the evaporator prepared by the method of one embodiment of the present disclosure are higher than the concentration and the malodorous intensity of the malodorous material in the evaporator prepared by the existing method, and the malodorous material is also detected in the same way in the functional evaluation result.

In addition, the concentration and malodorous intensity of the malodorous material prepared by the method of one embodiment of the present disclosure are similar to the concentration and malodorous intensity of the malodorous material measured for three types of used car, and the functional evaluation result is also shown to be the same.

Thus, when using the evaporator manufactured according to the method of one embodiment of the present disclosure, it is confirmed that the odor reflecting the field conditions may be reproduced.

As described above, exemplary embodiments of the present disclosure have been illustrated and described, but various modifications and other exemplary embodiments may be performed by those skilled in the art. The modifications and the other exemplary embodiments are all considered to be included in the appended claims, which fall within the spirit and scope of the present disclosure.

What is claimed is:

1. A method for pretreating an evaporator surface comprising:
    a step of preparing an inoculation of malodorous microorganisms;
    a step of preparing and pretreating an evaporator; and
    a step of immobilizing the malodorous microorganisms on the evaporator surface,
    wherein the step of preparing and pretreating the evaporator includes:
    a step of closing and sealing a refrigerant pipe of the evaporator;
    a step of treating a flowing stream of the evaporator of which the refrigerant pipe is closed and sealed; and
    a step of drying the evaporator of which the flowing stream is treated, and
    wherein the step of treating the flowing stream of the evaporator includes a step of installing the evaporator in a flowing stream treatment device and flowing tap water to accelerate odor reproduction by removing a surfactant component of the evaporator surface and aging a hydrophilic coating layer to facilitate attachment of microorganisms and gas adsorption.

2. The method for pretreating the evaporator surface of claim 1, wherein
    the step of preparing the inoculation of the malodorous microorganisms includes:
    a step of preparing the malodorous microorganisms;
    a step of preparing an LB broth liquid medium;
    a step of liquid-cultivating the malodorous microorganisms in the LB broth liquid medium; and
    a step of concentrating and recovering the cultivated malodorous microorganisms.

3. The method for pretreating the evaporator surface of claim 1, wherein:
    the step of treating the flowing stream of the evaporator further includes a step of treating the flowing stream to cleanse the evaporator surface, and
    the flowing stream treatment device includes a square box, an evaporator holder, a tap water inlet, and a tap water outlet.

4. The method for pretreating the evaporator surface of claim 1, wherein
    the step of immobilizing the malodorous microorganisms on the evaporator surface includes:

a step of preparing a liquid mixture of the malodorous microorganisms;

a step of spraying the liquid mixture of the malodorous microorganisms on the evaporator surface; and a step of drying the evaporator on which the liquid mixture of the malodorous microorganisms is sprayed.

5. The method for pretreating the evaporator surface of claim 4, wherein in the step of immobilizing the malodorous microorganisms on the evaporator surface, the step of spraying the liquid mixture and the step of drying the evaporator are sequentially repeated twice or more.

6. The method for pretreating the evaporator surface of claim 1, further comprising a step of producing a biofilm after the step of immobilizing the malodorous microorganisms on the evaporator surface.

7. The method for pretreating the evaporator surface of claim 6, wherein the step of producing the biofilm includes:

a step of preparing an LB broth nutrient;

a step of spraying the LB broth nutrient on the evaporator surface; and a step of drying and culturing the evaporator on which the LB broth nutrient is sprayed.

8. The method for pretreating the evaporator surface of claim 7, wherein in the step of producing the biofilm, the step of spraying the LB broth nutrient and the step of drying and culturing the evaporator are sequentially repeated twice or more.

\* \* \* \* \*